United States Patent [19]

Köhr

[11] Patent Number: 4,459,025

[45] Date of Patent: Jul. 10, 1984

[54] LIGHT-OPTICAL DETECTION DEVICE FOR SUSPENDED PARTICLES

[75] Inventor: Horst Köhr, Sulzburg, Fed. Rep. of Germany

[73] Assignee: Hekatron GmbH, Sulzburg, Fed. Rep. of Germany

[21] Appl. No.: 258,461

[22] Filed: Apr. 28, 1981

[30] Foreign Application Priority Data

Apr. 29, 1980 [DE] Fed. Rep. of Germany ....... 3016530

[51] Int. Cl.³ ................... G01N 21/51; G08B 17/10
[52] U.S. Cl. ..................................... 356/339; 340/630
[58] Field of Search ............................. 356/338–340; 340/628, 630; 250/574

[56] References Cited

U.S. PATENT DOCUMENTS

| 3,461,443 | 8/1969 | Vasel | 340/630 X |
| 3,727,056 | 4/1973 | Enemark | 340/630 X |
| 4,206,366 | 6/1980 | Marsocci et al. | 250/574 |

Primary Examiner—Bruce Y. Arnold
Attorney, Agent, or Firm—George E. Kersey

[57] ABSTRACT

The invention concerns a light-optical detection device for determining the concentration of suspended particles in a gaseous medium within a light-tight housing. The latter essentially is formed by a short cylinder sheath having two front-surface coverings that are formed by a base plate and by an opposite cover plate. Cylinders extend into said housing for receiving, respectively, a light source and a photocell. The cylinders have axes which intersect at right angles at the center of the device. The axis of the cylinder containing the light source essentially runs in the direction towards the diagonally opposite corner of the interior of the device.

10 Claims, 2 Drawing Figures

LIGHT-OPTICAL DETECTION DEVICE FOR SUSPENDED PARTICLES

BACKGROUND OF THE INVENTION

The invention concerns a light-optical detection device for determining the concentration of suspended particles in a gaseous medium within a light-tight housing. The latter essentially is formed by a short cylinder sheath having two front-surface coverings that are formed by a base plate and by an opposite cover plate. Cylinders extend into said housing, for receiving an optical detection system with a light source and a photocell.

Such a device is known from the West German Auslegeschrift No. 1 598 941. In this device, the cylinder with the photocell is arranged in the base plate and the cylinder with the light source is arranged in the cyinder sheath. In addition, a light trap is provided opposite the light source, and this light trap likewise extends as a cylinder outwardly away from the cylinder sheath. Because of this arrangement of the individual parts of the optical detection system, the structure has considerable spatial extension. Furthermore, it should be noted that the cylinders with the light source and the light trap cannot be moved relative to one another, since this would significantly impair the optical action of the light trap. If the light trap is to be optimally effective, both cylinders must be aligned precisely axial with respect to one another. Furthermore, with the known device, it is necessary that the base plate maintain an adequate distance from the mounting plane, which is generally formed by the ceiling of a room that is being monitored.

SUMMARY OF THE INVENTION

The invention is based on the aim of creating a light-optical detection device, which can be built more compactly and consequently smaller than the known device and whose internal construction furthermore guarantees that the axes of the optical detection system cannot move with respect to one another. According to the invention, this aim is achieved by the cylinder for the light source and the cylinder for the photocell being set into the base plate with their axes essentially making a right angle with one another. This is done in such a way that the two axes intersect approximately in the center of the interior space, and the axis of the cylinder containing the light source essentially runs in the direction towards the corner that is diagonally opposite to the cylinder.

This design deviates from the previously customary principle according to which the components of the optical detection system were on the one hand arranged axially and on the other hand were arranged diametrically. Instead of this, the axes of the optical detection system are set at a slant, essentially at 45° with respect to the axis of the cylinder sheath and consequently the entire device. In this way, it is possible to place both the light source and the photocell in a slanting arrangement in the base plate, that is to house them on a single component, which can easily be designed especially rigidly. The light trap, which was previously necessary, can be saved therewith, since here the effect is provided by the fact that the light emerging from the light source is directed in the diagonal direction into the diagonally opposite corner of the interior space of the device. Because of its design, the corner acts like a light trap with respect to the light source, since light from this corner cannot be reflected to the photocell. On the one hand, this results in a particularly rigid structure; furthermore, because the light source and the photocell are arranged on the base plate, this results in a particularly compact structure, which additionally even saves the light trap as a special projecting component.

An advantageous embodiment of the light-optical detection device consists in providing both the base plate and the cover plate with coaxial, circular recesses of the same diameter. The walls of these recesses on both sides enclose the front sides of the cylinder material. Here, distancing ribs running in the axial direction are affixed outwardly on the cylinder sheath. These distancing ribs extend beyond the front sides of the cylinder sheath and into the recesses. They are supported at least against the inside or outside wall of the recess. The distancing ribs facilitate simple and safe mounting of the cylinder sheath between the base plate and the cover plate, whereby the distancing ribs, because of their support at least against the inner or outer wall of the respective recess, take care that the cylinder sheath is held coaxial with respect to the recesses. Furthermore, the distancing ribs, which are affixed outwardly on the cylinder sheath, take care that the air which flows to the device is set into turbulence in the area of the distancing ribs, which assists in providing an adequate supply of suspended particles in the interior space of the device.

In order to fix uniquely the arrangement of the base plate, cylinder sheath, and cover plate with respect to one another as regards their rotational position, the distancing ribs differ in width and engage matching axial slots in the outer walls of the recesses.

Air, which in some circumstances may have a concentration of suspended particles, can thereby be better introduced into the interior space of the device, by slots being set into the bottom of the cover plate, where said slots lead into the respective recess, and by chambers being formed behind said slots, where said chambers extend up to the front side of the cylinder sheath and have openings that lead into the space between the cylinder sheath and the inner wall of the respective recess. The air is fed through the bottom of the cover plate, that is at first in the axial direction. As a result of the interaction with the air intakes at the upper front side of the cylinder sheath, a kind of chimney effect results, which intensifies the introduction of air into the interior space of the device. Air which passes by the device is in a certain sense sucked into the interior space of the device by means of these slots.

Furthermore, it is possible to provide additional opportunities for the entry of air, and specifically by arranging the chambers in the respective recess like segments with uniform distances from one another, whereby the gap areas form additional air intakes, which guide the air from the entry over the outer wall about the front side of the cylinder sheath and over the inner wall. In this way, more air intakes are created besides the chambers. These air intakes conduct the air beside the chambers through the recesses and about the front sides of the cylinder sheath, so that the inner space of the chamber becomes altogether easily accessible to the ambient air.

The entire device is suitably housed in a rotation-symmetric housing, which is provided with penetrations both opposite the free part of the cylinder sheath and opposite the slots. Here, the penetrations opposite the slots are placed in the axially running wall surface of a recess in the bottom of the housing, where said recess is directed towards the cover plate. With this design, the housing need not have regard for protruding cylinders, as is the case in the known device, so that the housing, too, has a relatively simple shape. In this way, any directional dependence of the device with respect to the approaching air is avoided from the very beginning. The penetrations, which are arranged in the axially running wall surface, will lie in a vertically situated wall surface, when the device is fastened to the ceiling of a room, as is normally the case. In a certain sense, these penetrations collect the passing air and conduct it to the interior space of the device.

DESCRIPTION OF THE DRAWINGS

A typical embodiment of the invention is shown in the figures. The following are shown.

DETAILED DESCRIPTION

Figure 1:
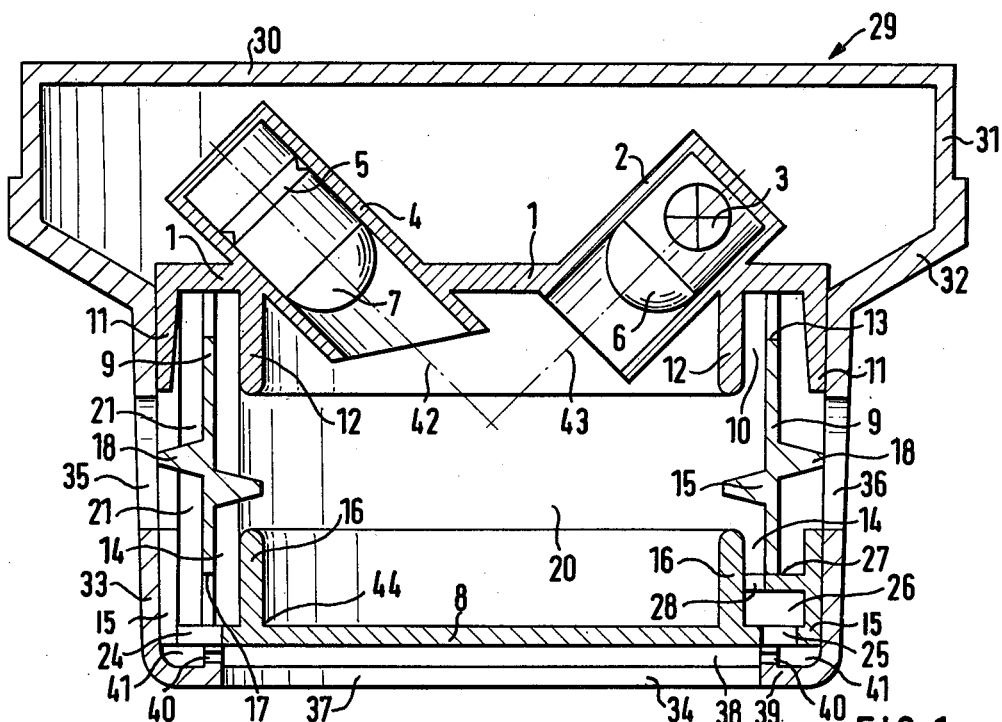
FIG. 1 shows a section through the device in the axial direction.

The light-optical detection device shown in FIG. 1 consists of the base plate 1, into which is set the cylinder 2 with the light source 3 and the cylinder 4 with the photocell 5. The optical lenses 6 and 7 are affixed respectively before the light source 3 and the photocell 5. The bottom plate 8 is arranged opposite the base plate 1, whereby the cylinder sheath 9 extends between the base plate 1 and the bottom plate 8.

At its outer rim, the base plate 1 is provided with the recess 10, which is formed by the outer wall 11 and the inner wall 12. The cylinder sheath 9, with its front side 13, extends into the recess 10. A similar design exists on the other side. The cover plate 8 is provided with the recess 14, which is formed by the outer wall 15 and the inner wall 16. The cylinder sheath 9, with its back side 17, extends into the recess 14. The cylinder sheath 9, approximately at its center, is provided with an outer annular ring 18 and an inner annular ring 19. These annular rings 18 and 19 have the purpose of deflecting as much as possible light that may be incident on the device and of shielding the interior space 20 of the device against the entry of light from the outside.

Distancing ribs 21 are affixed on the outside of the cylinder sheath 9. These distancing ribs 21 run in the axial direction. Both in the area of the front side 13 and the front side 17 of the cylinder sheath 9, the distancing ribs 21 go over into the cross beams 22 and 23. These cross beams 22 and 23 lie on the base of the recesses 10 and 14 and extend crosswise from the outer wall 11 to the inner wall 12 and respectively from the outer wall 15 to the inner wall 16. In this way, the distancing ribs 21 are fixed in their position with respect to the base plate 1 and the cover plate 8, and thereby hold the cylinder sheath 9 in a definite position with respect to the base plate 1 and the bottom plate 8. To simplify the figure, FIG. 1 shows only one distancing rib 21, but several such distancing ribs 21 are provided along the circumference of the cylinder sheath 9. On the basis of the embodiment shown in FIG. 2, there are four distancing ribs.

The slots 24, 25 are provided in the bottom of the cover plate 8, and they lead to the base of the recess 14. These slots 24, 25 are multiply affixed along the recess 14 (according to FIG. 2, there are six slots in all), and they always lead into a chamber 26, formed on the one hand by the bottom of the recess 14 laterally next to the slots 24, 25, and the walls 15 and 16 as well as the cover 27. The opening 28 is always provided in the cover 27, where said opening 28 leads from the chamber 26 into the space between the cylinder sheath 9 and the inner wall 16.

The device is enclosed by the housing 29. The housing 29 consists of the base 30 and a cylinder joining thereto, with its following cone section 32, which goes over into the pot-shaped wall 33. The pot-shaped wall is closed below by the pot-bottom 34. The penetrations 35, 36 are provided in the pot-shaped wall 33. These penetrations 35, 36 are situated opposite to the free part of the cylinder sheath 9, so that the air flowing through the penetrations 35, 36 can flow upwards and downwards along the cylinder sheath 9, until it reaches the recesses 10 and 14. There the air is deflected on the one hand about the front side 13 and on the other hand about the front side 17 of the cylinder sheath 9. It enters the interior space 20 of the device through the intermediate space between the cylinder sheath 9 and the inner wall 12 or respectively 16. This path is not blocked by the distancing rib 21, which is shown in the left part of FIG. 1, since the air can flow laterally past the distancing rib 21. The distancing rib is only a few millimeters wide. The free passage of the air can be seen clearly in the area of the front side 13 in the right part of FIG. 1.

The pot-bottom 34 has the recess 37, which is formed laterally by the axial wall surface 38 and in its center by the turntable 39. The penetrations 40 are affixed in the axial wall surface 38. From these penetrations 40, air can reach the free space 41 which is situated behind them. From this free space 41, air can penetrate through the slots 24, 25 into the chambers 26. From there, the air streams through the opening 28 into the interior space 20 of the device. The recess 37 and the axial wall surface 38 create a certain collection effect for the air that passes by the device. Because of this, the air is conducted into the penetrations 40, from which it then reaches the interior space 20 of the device, through the path that has been described above.

As FIG. 1 shows, the axis 42 of barrel 2 and the axis 43 of barrel 4 are directed so that the two axes intersect approximately in the center of the interior space. Here, the axis 42 of the barrel 2, which contains the light source 3, runs into the corner 44, which is formed by the cover plate 8 and the inner wall 16. The corner 44 thus acts as a light trap, which automatically results from the overall design of the device.

Figure 2:
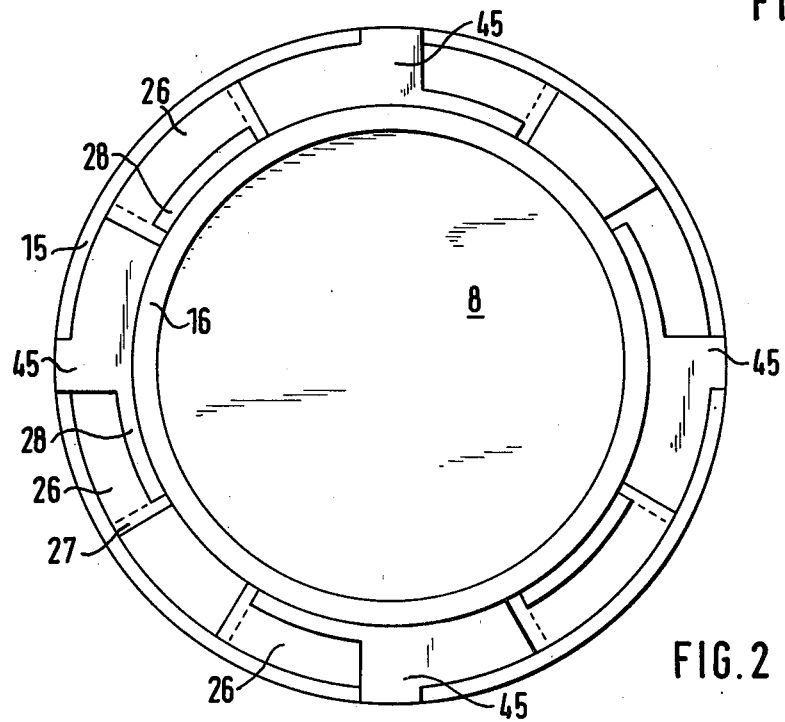
FIG. 2 shows a top view of the cover plate, as seen from the bottom plate.

FIG. 2 shows the cover plate 8 where, however, a change has been made in contrast to FIG. 1. In particular, with the cover plate 8 according to FIG. 1, axial slots 45 are provided so as to engage the distancing ribs 21. With the arrangement according to FIG. 1, on the other hand, the distancing ribs 21 contact the outer walls 11 and 15 from the inside. The arrangement according to FIG. 2 results in a definite position of the base plate 1, the cylinder sheath 9, and the cover plate 8 being achieved by means of the distancing ribs 21. For this purpose, the respective distancing ribs differ in width, and this width is matched to the slots 45. It is sufficient for only one of the slots 45 to be wider than the remaining three slots, and for a correspondingly wider distancing rib being matched to this wider slot.

FIG. 2 also shows how the chambers 26 are distributed on the base of the recess 14. As can be seen, six chambers 26 are provided in all, and they are closed at the top by the covers 27. Openings 28 are affixed in these covers 27. These openings 28 provide access from the chambers 26 to the intermediate space between the cylinder sheath 9 and the inner wall 16. The parts of the device described above, apart from the light source and the photocell, can be designed as injection-molded parts. This results in an especially compact and stable embodiment, since the two barrels 2 and 4 with the light source 3 and the photocell 5 are rigidly connected with the base plate 1 and furthermore are protected by the housing 29. Towards the outside, one sees only a rotation-symmetric body, so that twistings or bendings of any kind are scarcely possible, as would otherwise be possible in the case of protruding barrels and the like. The two barrels 2 and 4 are essentially arranged in a diagonal direction. This furthermore results in a space-saving arrangement, in which, as already mentioned, a special light trap can be dispensed with, since this light trap results automatically from the design.

While various aspects of the invention have been set forth by the drawings and specification, it is to be understood that the foregoing detailed description is for illustration only and that various changes in parts, as well as the substitution of equivalent constituents for those shown and described may be made without departing from the spirit and scope of the invention as set forth in the appended claims.

What is claimed is:

1. Apparatus for detecting the presence of particles suspended in a gaseous medium, comprising:
   a housing containing at least one corner where two surfaces intersect, and including a base member and an opposed cover member which are provided with coaxial circular recesses of the same diameter, said housing further including a cylindrical sheath having end portions which are enclosed by the inner and outer walls of said recesses, and distancing ribs affixed to said sheath that extend into said recesses;
   means for projecting an energy beam to said corner; and
   detection means having an axis which intersects the axis of said energy beam.

2. Apparatus as defined in claim 1 wherein said distancing ribs have different widths and engage matching axial slots in the outer walls of said recesses.

3. Apparatus as defined in claim 1 wherein slots are positioned in said cover member to lead into said recesses.

4. Apparatus as defined in claim 3 wherein said recesses contain chambers which are disposed in segmented fashion with a uniform distance from one to another and said cylindrical sheath is surrounded by an outer wall with gaps therein for the entry of said gaseous medium into said housing.

5. Apparatus as defined in claim 1 wherein said detection means and the projecting means are disposed within said housing so as to be rotationally symmetric and said housing is provided with penetrations opposite a portion of said cylindrical sheath and affixed in an axially disposed wall surface of a recess in the base of said housing.

6. Apparatus as defined in claim 1 wherein smoke particles are suspended in air, said housing is impervious to light, the projecting means comprises a light source in a cylinder on an upper surface of said housing, the detection means comprises a photocell in another cylinder on an upper surface of said housing, and the axes of said light source and said photocell intersect at approximately the middle of the interior of said housing.

7. Apparatus as defined in claim 6 wherein the upper surface of said housing is formed by a base member which forms a closure for a cylindrical sheath, and said housing is completed by a cover member which is positioned opposite said base plate and forms said corner by intersecting said cylindrical sheath.

8. Apparatus as defined in claim 1 wherein the intersection of the axis of said detection means forms substantially a right angle with the axis of said energy beam.

9. Apparatus as defined in claim 1 wherein said housing includes gaps therein which permit the entry of said gaseous medium into the interior thereof without the admission of external radiation.

10. Apparatus for detecting the presence of particles suspended in a gaseous medium, comprising
    a housing including a base member and an opposed cover member provided with coaxial circular recesses of the same diameter and including a cylindrical sheath, with affixed distancing ribs, having end portions enclosed by said recesses, said housing further including at least one corner where two surfaces intersect;
    means for projecting an energy beam into said housing to said corner; and
    detection means having an axis which intersects the axis of said energy beam.

* * * * *